US Patent Number: 4,798,621
Date of Patent: Jan. 17, 1989

Ackerson et al.

[54] SELECTIVE METHOD-OF-USE OF OXABICYCLOALKANES

[75] Inventors: Robert C. Ackerson, Wilmington, Del.; Takeshi Yuyama, Toride, Japan

[73] Assignee: E. I. Du Pont de Nemours and Company, Wilmington, Del.

[21] Appl. No.: 90,056

[22] Filed: Aug. 31, 1987

Related U.S. Application Data

[63] Continuation-in-part of Ser. No. 918,163, Oct. 10, 1986, abandoned.

[51] Int. Cl.$^4$ ...................... A01N 43/10; A01N 43/16
[52] U.S. Cl. .............................................. 71/90; 71/88
[58] Field of Search ....................................... 71/88, 90

[56] References Cited

U.S. PATENT DOCUMENTS 4,670,041  6/1987  Payne et al. ............................ 71/92

OTHER PUBLICATIONS

May et al., Chem. Abst., vol. 104 (1986), 124925r.

Primary Examiner—Catherine L. Mills

[57] ABSTRACT

This invention relates to a method for controlling the growth of undesired vegetation in paddy rice crops by applying an effective amount of an oxabicycloalkane herbicidal compound to the locus of paddy rice.

16 Claims, No Drawings

SELECTIVE METHOD-OF-USE OF OXABICYCLOALKANES

RELATED APPLICATION

This application is a continuation-in-part of my copending application U.S. Ser. No. 918,163 filed Oct. 10, 1986, now abandoned.

BACKGROUND OF THE INVENTION

This invention relates to a method for controlling the growth of undesired vegetation in paddy rice with an oxabicycloalkane herbicide.

U.S. Pat. No. 4,670,041 discloses oxabicycloalkanes and their use for controlling plant growth. There is no disclosure relating to the use of such oxabicycloalkanes for controlling plant growth for paddy rice.

SUMMARY OF THE INVENTION

This invention comprises a method for controlling the growth of undesired vegetation in a paddy rice crop by applying to the locus of the paddy rice crop a compound of Formula I.

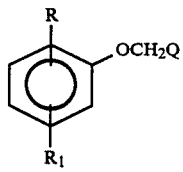

Formula I wherein
R is $CH_3$ or $CH_2CH_3$;
$R_1$ is $CH_3$, $CH_2CH_3$ or $CH(CH_3)_2$;
Q is

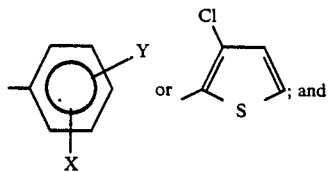

X and Y are independently H, F, Cl or $CH_3$.

Preferred for reasons of more efficient weed control and/or better crop tolerance are:
1. The method wherein the crop is transplanted japonica rice.
2. The method wherein the crop is transplanted indica rice.
3. The method wherein among the weeds controlled is barnyardgrass.

Specifically preferred for reasons of most efficient weed control and/or better crop tolerance is the method wherein the compound of Formula I is selected from the group consisting of:
2-exo-[(2-methylphenyl)methoxy]-1-methyl-4-(1-methylethyl)-7-oxabicyclo[2.2.1]heptane;
2-exo-[(2,6-dichlorophenyl)methoxy]-1-methyl-4-(1-methylethyl)-7-oxabicyclo[2.2.1]heptane;
2-exo-[(3-chloro-2-thienyl)methoxy]-1-methyl-4-(1-methylethyl)-7-oxabicyclo[2.2.1]heptane;
2-exo-[(2-fluorophenyl)methoxy]-1,4-diethyl-7-oxabicyclo[2.2.1]heptane;
2-exo[(2,6-dichlorophenyl)methoxy]-1,4-diethyl-7-oxabicyclo[2.2.1]heptane;
2-exo-[(2,6-dichlorophenyl)methoxy]-1-methyl-4-ethyl-7-oxabicyclo[2.2.1]heptane;
2-exo-[(2-fluorophenyl)methoxy]-1-methyl-4-(1-methyethyl)-7-oxabicyclo[2.2.1]heptane;
2-exo-[(2,6-dichlorophenyl)methoxy]-1-ethyl-4-methyl-7-oxabicyclo[2.2.1]heptane;
2-exo-[(2,3-difluorophenyl)methoxy]-1-methyl-4-(1-methylethyl)-7-oxabicyclo[2.2.1]heptane;
2-exo-[(2,4-difluorophenyl)methoxy]-1-methyl-4-(1-methylethyl)-7-oxabicyclo[2.2.1]heptane;
2-exo-[(2,5-difluorophenyl)methoxy]-1-methyl-4-(1-methylethyl)-7-oxabicyclo[2.2.1]heptane; and
2-exo-[(3,4-difluorophenyl)methoxy]-1-methyl-4-(1-methylethyl)-7-oxabicyclo[2.2.1]heptane.

This invention further comprises the method-of-use for selectively controlling gramineous weeds of a paddy rice field comprising applying an effective amount of a compound described above or mixtures thereof to the locus of the paddy rice crop.

DETAILED DESCRIPTION OF THE INVENTION

Compounds of Formula I are known in the art. They can be prepared according to processes described in U.S. Pat. No. 4,670,041. All stereoisomers (diastereomers and enantiomers); endo and exo forms; and mixtures thereof are within the scope of the present invention. The various individual isomeric forms and various combinations of the derivatives usually have some difference in herbicidal or plant growth control properties.

FORMULATIONS

The method of this invention can be conveniently carried out by formulating a compound of Formula I in the conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

|  | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following Examples, all parts are by weight unless otherwise indicated.

EXAMPLE 1

| Wettable Powder | |
| --- | --- |
| 2-exo-[(2-methylphenyl)methoxy]-1-methyl-4-(1-methylethyl)-7-oxabicyclo[2.2.1]heptane | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 2

| Granule | |
| --- | --- |
| Wettable Powder of Example 1 | 5% |
| attapulgite granules (U.S.S. 20 to 40 mesh; 0.84–0.42 mm) | 95% |

A slurry of wettable powder containing 25% solids is sprayed on the surface of attapulgite granules in a double-cone blender. The granules are dried and packaged.

EXAMPLE 3

| Extruded Pellet | |
| --- | --- |
| 2-exo-[(2-methylphenyl)methoxy]-1-methyl-4-(1-methylethyl)-7-oxabicyclo[2.2.1]heptane | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 4

| Low Strength Granule | |
| --- | --- |
| 2-exo-[(2-methylphenyl)methoxy]-1-methyl-4-(1-methylethyl)-7-oxabicyclo[2.2.1]heptane | 0.1% |
| attapulgite granules (U.S.S. 20 to 40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 5

| Low Strength Granule | |
| --- | --- |
| 2-exo-[(2-methylphenyl)methoxy]-1-methyl-4-(1-methylethyl)-7-oxabicyclo[2.2.1]heptane | 1% |
| N,N—dimethylformamide | 9% |
| attapulgite granules (U.S.S. 20 to 40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 6

| Wettable Powder | |
| --- | --- |
| 2-exo-[(2-methylphenyl)methoxy]-1-methyl-4-(1-methylethyl)-7-oxabicyclo[2.2.1]heptane | 40% |

| Wettable Powder | |
|---|---|
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 7

| Emulsifiable Concentrate | |
|---|---|
| 2-exo-[(2-methylphenyl)methoxy]-1-methyl-4-(1-methylethyl)-7-oxabicyclo[2.2.1]heptane | 35% |
| blend of polyalcohol carboxylic esters and oil soluble petroleum sulfonates | 6% |
| xylene | 59% |

The ingredients are combined and filtered to remove undissolved solids. The product can be used directly, extended with oils, or emulsified in water.

EXAMPLE 8

| Dust | |
|---|---|
| 2-exo-[(2-methylphenyl)methoxy]-1-methyl-4-(1-methylethyl)-7-oxabicyclo[2.2.1]heptane | 10% |
| attapulgite | 10% |
| Pyrophyllite | 80% |

The active ingredient is blended with attapulgite and then passed through a hammer-mill to produce particles and then passed through a hammer-mill to produce particles substantially all below 200 microns. The ground concentrate is then blended with powdered pyrophyllite until homogeneous.

EXAMPLE 9

| Wettable Powder | |
|---|---|
| 2-exo-[(2-methylphenyl)methoxy]-1-methyl-4-(1-methylethyl)-7-oxabicyclo[2.2.1]heptane | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

UTILITY

Test results indicate that the compounds of the present invention are highly active preemergent or postemergent herbicides or plant growth regulators. They have utility for selective weed control in paddy rice fields containing japonica or indica rice.

Compounds of this invention are particularly useful for the control of weeds in paddy rice. They may be applied postemergence to paddy rice or to rice from which the flood has been removed. They may also be applied to paddy rice after transplanting as a spray or granule. The application may be made from 3 to 10 days after transplanting.

Rates of 16 to 1500 g/ha will provide weed control. The compounds are particularly useful for the control of barnyardgrass (*Echinochloa crus-galli*), a pernicious weed in rice culture, but may also provide complete or partial control of other weeds, particularly gramineous weeds, in rice.

Compounds

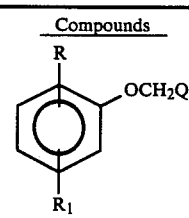

| Compound | R | $R_1$ | Q |
|---|---|---|---|
| 1 (exo) | $CH_3$ | $CH(CH_3)_2$ | 2-methylphenyl |
| 2 (exo) | $CH_3$ | $CH(CH_3)_2$ | 2,6-dichlorophenyl |
| 3 (exo) | $CH_3$ | $CH(CH_3)_2$ | 3-chloro-2-thienyl |
| 4 (exo) | $CH_2CH_3$ | $CH_2CH_3$ | 2-fluorophenyl |
| 5 (exo) | $CH_2CH_3$ | $CH_2CH_3$ | 2,6-dichlorophenyl |
| 6 (exo) | $CH_3$ | $CH_3CH_2$ | 2,6-dichlorophenyl |
| 7 (exo) | $CH_3$ | $CH(CH_3)_2$ | 2-fluorophenyl |
| 8 (exo) | $CH_2CH_3$ | $CH_3$ | 2,6-dichlorophenyl |
| 9 (exo) | $CH_3$ | $CH(CH_3)_2$ | 2,3-difluorophenyl |
| 10 (exo) | $CH_3$ | $CH(CH_3)_2$ | 2,4-difluorophenyl |
| 11 (exo) | $CH_3$ | $CH(CH_3)_2$ | 2,5-difluorophenyl |

EXAMPLE 10

Waxed paper cups with top surface area of 100 $cm^2$ were filled with Sassafras sandy loam soil. Japonica variety M101 and indica variety Starbonnet were directly seeded, covered with 1 cm of soil, and the soil kept moist but not flooded until the 2.0 leaf stage (LS) of rice. One day before application, the soil in each cup was flooded to a depth of 3 cm. The compounds were dissolved in an acetone-based solvent and directly applied to the water. Fresh weights of the top growth were determined 10–14 days after application. Results are shown in Table 1.

When applied to the paddy water at 2.0 to 2.2 leaf-stage of direct-seeded rice, Compound 1 caused 40–45% crop injury (reduction of fresh weights) to both japonica and indica rice at 125 g a.i./ha. No injury was observed at 30 g/ha. However, in a separate test previously carried out, a different sample of Compound 1 did not show any phytotoxicity on japonica rice at 125 g rate. Compound 2 was tolerant to japonica rice, showing no phytotoxicity at the rates up to 500 g/ha.

In the tables that follow, LS is leaf stage.

TABLE 1

Rice Tolerance in Direct-Seeded Japonica and Indica Rice (2.0–2.2 LS)

| | % Crop Injury (g/ha) | | | | | | | |
|---|---|---|---|---|---|---|---|---|
| | Japonica (M101) | | | | Indica (Starbonnet) | | | |
| Compound | 30 | 125 | 500 | 2000 | 30 | 125 | 500 | 2000 |
| 1 | 0 | 45 | 85 | 85 | 0 | 40 | 75 | 85 |
| 1 (different sample) | 0 | 0 | 50 | 0 | 0 | 60 | 80 | 85 |
| 2 | 0 | 0 | 0 | 40 | 0 | 40 | 0 | 40 |

EXAMPLE 11

Airlite pots with top surface area of 200 cm² were filled with Sassafras sandy loam. About 1500 ml of water were added to each pot to bring the water level to a point 1 cm above the soil surface. Japonica and Indica rice seedlings were transplanted. Also, a number of barnyardgrass (*Echinochloa crus-galli*) seeds were added to separate pots. At the same time, seedlings or tubers of the following species were transplanted into the muddy soil in the third pot: water plantain (*Alisma trivale*), Scirpus (*Scirpus paludosus*), Cyperus (*Cyperus esculentus*) and arrowhead (*Sagittaria latifolia*). The weed species selected for this test are of economic importance in major rice-growing areas or represent genera of important rice weeds. The chemical treatments were applied within hours after transplanting an additional species: water chestnut (Eleocharis spp.) to the pot seeded with barnyardgrass and adding water up to 3 cm. The pots were then maintained in the greenhouse. Rates of application and plant response ratings made 17-21 days after treatment are summarized in Table 2.

Compound 1 showed excellent (≧90%) barnyardgrass control at rates as low as 16 g a.i./ha, as did Compound 1 (different sample). There were no significant crop injuries seen with any of these three analogs including Compound 1 at rates up to 63 g a.i./ha. Compound 2 looked comparable to Compound 1 only at 63 g (95% control).

TABLE 2
Herbicidal Activity Study
(4 DAT of rice/0.5-1.0 LS of BYG)

| Compound | Rate (g a.i./ha) | % Injury or Control | | | | | | | |
|---|---|---|---|---|---|---|---|---|---|
| | | J | I | BYG | WC | AH | SC | CY | WP |
| 1 | 63 | 5 | 7 | 97 | — | 0 | 50 | 0 | 65 |
| | 30 | 0 | 0 | 92 | — | 0 | 0 | 0 | 35 |
| | 16 | 0 | 0 | 95 | — | 0 | 0 | 0 | 0 |
| 1 (different sample) | 30 | 10 | 10 | 100 | 0 | 0 | 0 | 35 | 0 |
| | 16 | 15 | 33* | 92 | 0 | 0 | 30 | 15 | 0 |
| | 8 | 0 | 0 | 75 | 0 | 0 | 35 | 0 | 0 |
| 2 | 63 | 0 | 0 | 95 | — | 0 | 0 | 0 | 75 |
| | 30 | 0 | 0 | 70 | — | 12 | 0 | 0 | 75 |
| | 16 | 0 | 0 | 77 | — | 0 | 0 | 0 | 50 |

*Note: appeared to be diseased
J = Japonica Rice
I = Indica Rice
BYG = Barnyardgrass
WC = Water chestnut
AH = Arrowhead
SC = Scirpus
CY = Cyperus
WP = Water Plantain

EXAMPLE 12

Waxed paper cups with top surface area of 100 cm², were filled with Sassafras sandy loam soil and sown with barnyardgrass, which was kept moist until seedlings began to emerge. Water was then added to a 3 cm depth and applications were made at rates and leaf stages described in Tables 3 and 4. Ratings were done 14 days after application.

In the Table 3 results barnyardgrass growth was accelerated by very high temperature conditions during the test period, which temperature was higher than in Example 11. However, Compound 1 still showed relatively high activity. The compounds and rates that gave 85% and better BYG control are 30-63 g at 1-1.5 LS, 63-125 g at 2-2.5 LS and 250 g at 3-3.5 LS with Compound 1, and 63 g at 1-1.5 LS, 125 g at 2-25 LS with Compound 2. Also Compound 1 was much better than standard products, namely, butachlor and quinclorac (BAS-514H) in the gram for gram comparison.

(Table 4) Similar results were obtained in the additional study for BYG activity comparison as discussed in Table 3. Compound 1 was the most active. These analogs were still better than butachlor in gram for gram comparison.

A later BYG study is shown in Table 5.

TABLE 3
Barnyardgrass Response in Relation to Application Timing

| Compound | Application Timing (LS of BYG) | % BYG Control (g a.i./ha) | | | | | | | |
|---|---|---|---|---|---|---|---|---|---|
| | | 8 | 16 | 30 | 63 | 125 | 250 | 500 | 1000 |
| 1 | 1-1.5 | 40 | 57 | 100 | 100 | — | — | — | — |
| | 2-2.5 | — | 50 | 70 | 85 | 90 | — | — | — |
| | 3-3.5 | — | — | 50 | 72 | 82 | 87 | — | — |
| 1 (different sample) | 1 | — | — | — | 100 | 100 | 100 | 100 | — |
| | 2 | — | — | — | — | 100 | 99 | 100 | 100 |
| | 3 | — | — | — | — | — | 92 | 97 | 50* |
| 2 | 1-1.5 | 25 | 50 | 65 | 100 | — | — | — | — |
| | 2-2.5 | — | 10 | 37 | 62 | 92 | — | — | — |
| | 3-3.5 | — | — | 0 | 20 | 47 | 55 | — | — |
| butachlor | 1-1.5 | — | — | — | 25 | 65 | 85 | 95 | — |
| | 2-2.5 | — | — | — | — | 60 | 75 | 90 | 95 |
| quinclorac | 3-3.5 | — | — | — | — | 20 | 47 | 72 | 92 |

*Mistreatments most likely.

TABLE 4
BYG Control Activity
(Additional Study)

| Compound | Application Timing (LS of BYG) | % BYG Control (g a.i./ha) | | | | | |
|---|---|---|---|---|---|---|---|
| | | 16 | 30 | 63 | 125 | 250 | 500 |
| 1 | 1 | 99 | 0* | 99 | 100 | — | — |
| | 2 | 67 | 82 | 90 | 95 | — | — |
| | 3 | 47 | 62 | 62 | 80 | — | — |

*Likely mistreatment.

TABLE 5
BYG Control Activity
(Additional Study)

| Compound | Application Timing (LS of BYG) | % BYG Control (g a.i./ha) | | | | | | | |
|---|---|---|---|---|---|---|---|---|---|
| | | 8 | 16 | 30 | 63 | 125 | 250 | 500 | 1000 |
| 1 | 1 | 77 | 98 | 100 | 100 | — | — | — | — |
| | 2 | — | — | 92 | 95 | 96 | 96 | — | — |
| | 3 | — | — | — | — | 92 | 98 | 99 | 99 |
| 2 | 1 | 77 | 95 | 98 | 100 | — | — | — | — |
| | 2 | — | — | 67 | 92 | 95 | 98 | — | — |
| | 3 | — | — | — | — | 87 | 96 | 99 | 99 |

EXAMPLE 13

Waxed paper cups with a top surface area of 100 cm² were filled with Sassafras sandy loam soil. Water was added to each cup to a level of 1 cm over the soil. Then, japonica rice (M101) seeds, which had been soaked 24 hours in water, were placed in the cup, approximately 6 seeds per cup. Rates of application were made the day after seeding (1 DAS), 1 and 2 leaf stage of the rice plants. Ratings were made 14 days after application. The results are summarized in Table 5.

As shown in Table 6, Compound 1 was toxic to direct water-seeded rice when applied early emergence. Compound 2 was a little less toxic than Compound 1.

TABLE 6

Crop Tolerance in Direct Water-Seeded Japonica Rice (M101)

| Compound | Application Timing | % Injury | | | | | |
|---|---|---|---|---|---|---|---|
| | | (g a.i./ha) | | | | | |
| | | 30 | 63 | 125 | 250 | 500 | 1000 |
| 1 | 1 DAS | 100 | 100 | 100 | 100 | — | — |
| | 1 LS | — | 100 | 100 | 100 | 100 | — |
| | 2 LS | — | — | 75 | 82 | 90 | 92 |
| 2 | 1 DAS | 80 | 93 | 100 | 100 | — | — |
| | 1 LS | — | 90 | 98 | 100 | 100 | — |
| | 2 LS | — | — | 15 | 60 | 70 | 70 |
| butachlor | 1 DAS | — | — | — | 100 | 100 | — |
| | 1 LS | — | — | — | — | 98 | 98 |
| quinclorac | 2 LS | — | — | — | 0 | 0 | — |
| | | | 2000 | | | 4000 | |
| | | (g a.i./ha) | | | | | |
| molinate | 1 DAS | | 71 | | | 26 | |
| | 1 LS | | 20 | | | 91 | |
| | 2 LS | | 15 | | | 25 | |

EXAMPLE 14

Sixteen cm diameter Airlite plastic pots were partially filled with Tama silt loam soil and the soil saturated with water. Japonica and Indica rice seedlings at the 2.0 to 2.5 leaf stage were transplanted into ⅓ of the pots. Into another third of the pots were transplanted seedling or sprouted tubers of water plantain (*Alisma trivale*), Scirpus (*Scirpus paludosus*), Cyperus (*Cyperus esculentus*), and arrowhead (Sagittaria spp.). The remaining pots were planted with barnyardgrass (*Echinochloa crus-galli*) seed and sprouted tubers of water chestnut (Eleocharis spp.). These weeds all represent major rice weeds or genera of weeds important in rice. Three to four days after planting, the water level was raised to 3 cm (about 1200 ml/pot) and maintained at this level throughout the test. Chemical treatments were applied directly to the paddy water, within 24 hours of raising the water, after being formulated in a non-phytotoxic solvent. The pots were maintained in the greenhouse. Rates of application and plant response ratings made 21 days after treatment are summarized in Table 7.

EXAMPLE 15

Waxed paper cups with a top surface of 100 cm$^2$ were partially filled with Tama silt loam soil. Either barnyardgrass or japonica rice seeds were planted into the soil in each pot, which was kept moist until the seedlings had reached the one leaf stage. Water was then added to a 3 cm depth and applications of chemical were made directly to the water after being formulated in a non-phytoxic solvent. Treatments were made at the 1.5–2.0 leaf stage of barnyardgrass and 1 leaf stage of rice. Visual evaluations of weed control and crop injury were made 14 days after application. The test results are summarized in Table 8.

TABLE 8

| COMPOUND | RATE g/ha | % Control | |
|---|---|---|---|
| | | RICE | BARNYARD GRASS |
| *1 | 8 | 0 | 0 |
| | 32 | 0 | 65 |
| | 125 | 0 | 95 |
| | 500 | 0 | 100 |
| *1 | 8 | 0.0 | 0.0 |
| | 32 | 0.0 | 20.0 |
| | 125 | 6.6 | 91.6 |
| | 500 | 40.0 | 98.3 |
| *1 | 8 | — | 40 |
| | 32 | 11 | 78 |
| | 125 | 22 | 100 |
| | 500 | 79 | 100 |
| | 1000 | 86 | — |
| *1 | 8 | — | 40 |
| | 32 | 0 | 80 |
| | 125 | 20 | 100 |
| | 500 | 65 | 100 |
| | 1000 | 75 | — |
| 2 | 8 | — | 0 |
| | 32 | 0 | 83 |
| | 125 | 0 | 98 |
| | 500 | 0 | 100 |
| | 1000 | 12 | — |
| 3 | 8 | — | 0 |
| | 32 | 12 | 93 |
| | 125 | 4 | 98 |
| | 500 | 46 | 100 |
| | 1000 | 79 | — |
| 4 | 8 | — | 50 |
| | 32 | 0 | 100 |
| | 125 | 29 | 100 |
| | 500 | 86 | 100 |
| | 1000 | 92 | — |

TABLE 7

| Compound | GM/HA | % Injury or Control | | | | | | |
|---|---|---|---|---|---|---|---|---|
| | | Japonica Rice | Indica Rice | Barnyard-grass | Water Chestnut | Arrowhead | Scirpus | Cyperus | Water Plantain |
| 7 | 1000 | 40 | 70 | 100 | 0 | 0 | 70 | 75 | 80 |
| | 500 | 20 | 80 | 100 | 0 | 0 | 40 | 50 | 70 |
| | 250 | 0 | 40 | 100 | 0 | 0 | 0 | 40 | 0 |
| | 125 | 0 | 30 | 100 | 0 | 0 | 0 | 0 | 0 |
| | 64 | 0 | 0 | 100 | 0 | 0 | 0 | 0 | 0 |
| 9 | 1000 | 40 | 60 | 100 | 0 | 0 | 0 | 40 | 40 |
| | 500 | 30 | 40 | 90 | 0 | 0 | 0 | 0 | 0 |
| | 250 | 0 | 0 | 80 | 0 | 0 | 0 | 0 | 0 |
| | 125 | 0 | 0 | 80 | 0 | 0 | 0 | 0 | 0 |
| | 64 | 0 | 0 | 100 | 0 | 0 | 0 | 0 | 0 |
| 10 | 1000 | 60 | 70 | 100 | 75 | 0 | 0 | 0 | 0 |
| | 500 | 30 | 30 | 100 | 0 | 0 | 0 | 0 | 0 |
| | 250 | 20 | 20 | 90 | 0 | 0 | 0 | 0 | 0 |
| | 125 | 0 | 0 | 90 | 0 | 0 | 0 | 0 | 0 |
| | 64 | 0 | 0 | 90 | 0 | 0 | 0 | 0 | 0 |
| 11 | 1000 | 30 | 50 | 100 | 0 | 0 | 60 | 0 | 0 |
| | 500 | 0 | 10 | 100 | 0 | 0 | 0 | 0 | 0 |
| | 250 | 0 | 10 | 90 | 0 | 0 | 0 | 0 | 0 |
| | 125 | 0 | 0 | 100 | 0 | 0 | 0 | 0 | 0 |
| | 64 | 0 | 0 | 90 | 0 | 0 | 0 | 0 | 0 |

TABLE 8-continued

| COMPOUND | RATE g/ha | % Control RICE | BARNYARD GRASS |
|---|---|---|---|
| 5 | 8 | — | 0 |
|  | 32 | 0 | 40 |
|  | 125 | 0 | 98 |
|  | 500 | 27 | 100 |
|  | 1000 | 22 | — |
| 6 | 8 | — | 0 |
|  | 32 | 15 | 30 |
|  | 125 | 4 | 95 |
|  | 500 | 62 | 100 |
|  | 1000 | 44 | — |
| 7 | 8 | — | 50 |
|  | 32 | 0 | 90 |
|  | 125 | 0 | 100 |
|  | 500 | 60 | 100 |
|  | 1000 | 75 | — |
| *8 | 8 | 0 | 0.0 |
|  | 32 | 0 | 16.6 |
|  | 125 | 0 | 91.6 |
|  | 500 | 0 | 96.6 |
| *8 | 8 | 0 | 0 |
|  | 32 | 0 | 10 |
|  | 125 | 0 | 80 |
|  | 500 | 0 | 100 |
| 9 | 8 | — | 0 |
|  | 32 | 0 | 35 |
|  | 125 | 0 | 95 |
|  | 500 | 50 | 100 |
|  | 1000 | 65 | — |

*results of separate tests

What is claimed is:

1. The method for controlling the growth of undesired vegetation in a paddy rice crop which comprises applying to the locus of the paddy rice crop an effective amount of a compound of the formula:

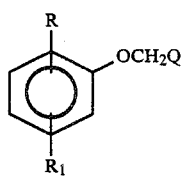

wherein
R is $CH_3$ or $CH_2CH_3$;
$R_1$ is $CH_3$, $CH_2CH_3$ or $CH(CH_3)_2$;
Q is

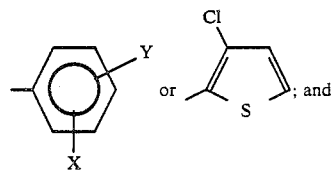

X and Y are independently H, F, Cl or $CH_3$.

2. The method of claim 1 wherein the crop is transplanted japonica rice.

3. The method of claim 1 wherein the crop is transplanted indica rice.

4. The method of claim 1 wherein the undesired vegetation controlled is barnyardgrass.

5. The method of claim 1 wherein the compound is 2-exo-[(2-methylphenyl)methoxy]-1-methyl-4-(1-methylethyl)-7-oxabicyclo[2.2.1]heptane.

6. The method of claim 1 wherein the compound is 2-exo-[(2,6-dichlorophenyl)methoxy]-1-methyl-4-(1-methylethyl)-7-oxabicyclo[2.2.1]heptane.

7. The method claim 1 wherein the compound is 2-exo-[(3-chloro-2-thienyl)methoxy]-1-methyl-4-(1-methylethyl)-7-oxabicyclo[2.2.1]heptane.

8. The method of claim 1 wherein the compound is 2-exo-[(2-fluorophenyl)methoxy]-1,4-diethyl-7-oxabicyclo[2.2.1]heptane.

9. The method of claim 1 wherein the compound is 2-exo-[(2,6-dichlorophenyl)methoxy]-1,4-diethyl-7-oxabicyclo[2.2.1]heptane.

10. The method of claim 1 wherein the compound is 2-exo-[(2,6-dichlorophenyl)methoxy]-1-methyl-4-ethyl-7-oxabicyclo[2.2.1]heptane.

11. The method of claim 1 wherein the compound is 2-exo-[(2-fluorophenyl)methoxy]-1-methyl-4-(1-methylethyl)-7-oxabicyclo[2.2.1]heptane.

12. The method of claim 1 wherein the compound is 2-exo-[(2,6-dichlorophenyl)methoxy]-1-ethyl-4-methyl-7-oxabicyclo[2.2.1]heptane.

13. The method of claim 1 wherein the compound is 2-exo-[(2,3-difluorophenyl)methoxy]-1-methyl-4-(1-methylethyl)-7-oxabicyclo[2.2.1]heptane.

14. The method of claim 1 wherein the compound is 2-exo-[(2,4-difluorophenyl)methoxy]-1-methyl-4-(1-methylethyl)-7-oxabicyclo[2.2.1]heptane.

15. The method of claim 1 wherein the compound is 2-exo-[(2,5-difluorophenyl)methoxy]-1-methyl-4-(1-methylethyl)-7-oxabicyclo[2.2.1]heptane.

16. The method of claim 1 wherein the compound is 2-exo-[(3,4-difluorophenyl)methoxy]-1-methyl-4-(1-methylethyl)-7-oxabicyclo[2.2.1]heptane.

* * * * *